(12) United States Patent
Umekawa

(10) Patent No.: US 12,303,317 B2
(45) Date of Patent: May 20, 2025

(54) RADIATION IMAGING APPARATUS, RADIATION IMAGING SYSTEM, AND CONTROL METHOD OF RADIATION IMAGING APPARATUS

(71) Applicant: CANON KABUSHIKI KAISHA, Tokyo (JP)

(72) Inventor: Kazuaki Umekawa, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 450 days.

(21) Appl. No.: 17/720,173

(22) Filed: Apr. 13, 2022

(65) Prior Publication Data
US 2022/0338831 A1    Oct. 27, 2022

(30) Foreign Application Priority Data
Apr. 22, 2021    (JP) .................. 2021-072810

(51) Int. Cl.
*A61B 6/00*    (2024.01)
*A61B 6/42*    (2024.01)

(52) U.S. Cl.
CPC ............ *A61B 6/542* (2013.01); *A61B 6/4233* (2013.01); *A61B 6/4291* (2013.01); *A61B 6/547* (2013.01); *A61B 2560/0276* (2013.01)

(58) Field of Classification Search
CPC ..... A61B 6/542; A61B 6/4233; A61B 6/4291; A61B 6/547; A61B 2560/0276
See application file for complete search history.

(56) References Cited

U.S. PATENT DOCUMENTS

| | | | | |
|---|---|---|---|---|
| 6,157,700 A * | 12/2000 | Sako | ............... | A61B 6/06 378/98.12 |
| 6,480,574 B2 * | 11/2002 | Goto | ............... | A61B 6/4291 378/154 |
| 2004/0101101 A1 | 5/2004 | Hirai | | |
| 2011/0243305 A1 * | 10/2011 | Tada | ............... | A61B 6/583 378/207 |
| 2012/0241629 A1 * | 9/2012 | Kuwabara | ............ | A61B 6/4291 250/362 |
| 2015/0030129 A1 * | 1/2015 | Tajima | ............ | A61B 6/4291 378/62 |
| 2015/0131784 A1 | 5/2015 | Tajima | | |
| 2022/0338831 A1 * | 10/2022 | Umekawa | ............ | A61B 6/4283 |

FOREIGN PATENT DOCUMENTS

JP    2014039792 A    3/2014

* cited by examiner

*Primary Examiner* — Oommen Jacob
(74) *Attorney, Agent, or Firm* — Canon U.S.A., Inc. IP Division

(57) ABSTRACT

A radiation imaging apparatus includes a pixel array including, in an imaging region where a plurality of pixels is arranged in a matrix, a detection pixel group in which a plurality of detection pixels is arranged in a row direction, and a control unit configured to control imaging. A grid having a stripe structure in which a radiation transmissive layer and a radiation absorption layer that are strip-shaped and extend in a first direction are alternately arranged in a second direction is disposed and can be used in the radiation imaging apparatus. The radiation imaging apparatus further includes a determination unit configured to determine whether a mode in which the imaging using signals from the detection pixel group is controlled is executable by the control unit, based on information about an angle between the row direction and the first direction.

12 Claims, 6 Drawing Sheets

EXEMPLARY EMBODIMENT

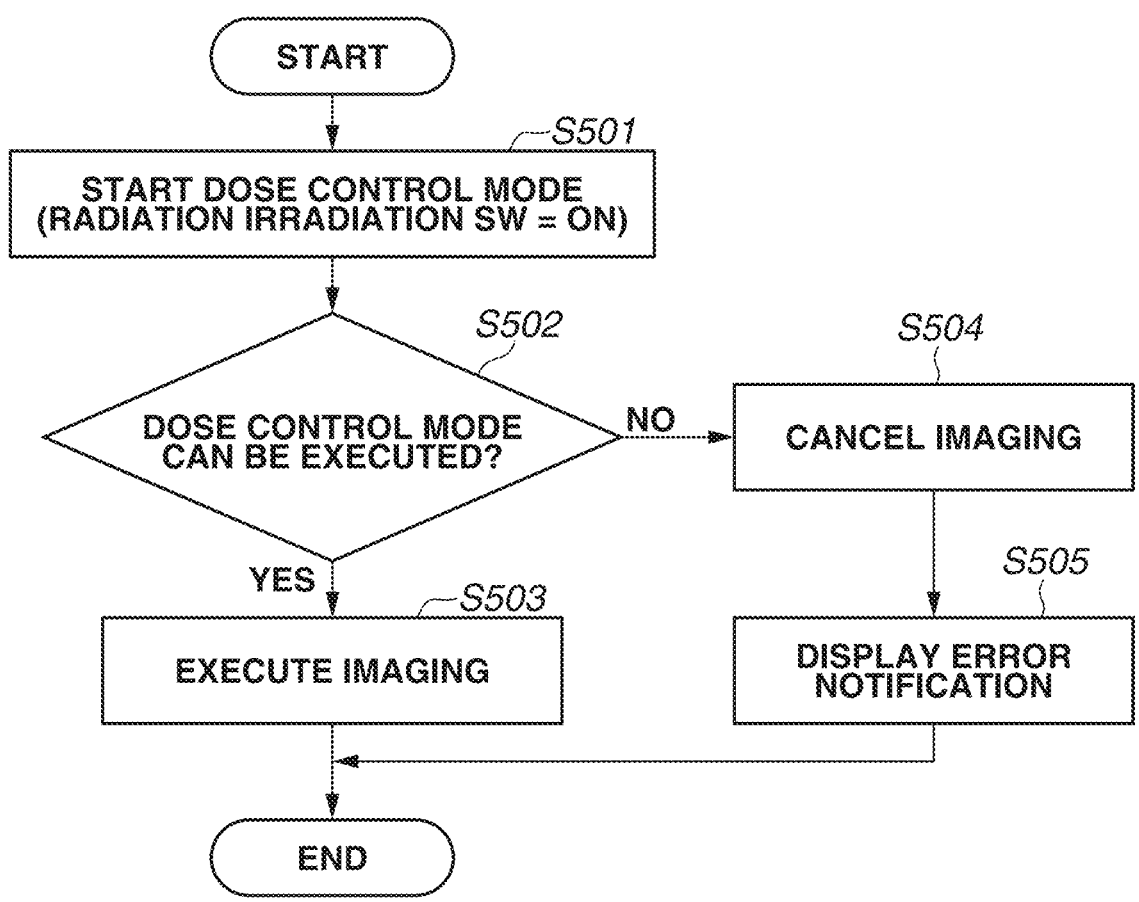

RADIATION IMAGING APPARATUS, RADIATION IMAGING SYSTEM, AND CONTROL METHOD OF RADIATION IMAGING APPARATUS

BACKGROUND OF THE INVENTION

Field of the Invention

The present invention relates to a radiation imaging apparatus, a radiation imaging system, and a control method of the radiation imaging apparatus.

Description of the Related Art

Radiation imaging apparatuses using a sensor panel for detecting radiation such as X-rays are used in fields of industry, medical care, and the like. In recent years, radiation imaging apparatuses which multiple functions have been contemplated. As one of such cases, a radiation imaging apparatus having a built-in function of monitoring irradiation of radiation has been suggested. This function enables the radiation imaging apparatus to detect, for example, the timing of starting irradiation of radiation from a radiation source, the timing to stop the irradiation of the radiation, and a dose or integrated dose of the radiation. The radiation imaging apparatus can perform automatic exposure control (AEC), by detecting an integrated dose of radiation passing through a subject, and stopping the irradiation of the radiation by the radiation source at the time when the detected integrated dose reaches an appropriate amount. In order to realize this function, some of these known radiation imaging apparatuses include dose detection pixels for detecting an irradiated dose separately from pixels for capturing a radiation image.

Meanwhile, in radiation imaging, scattered rays are generated when radiation passes through an object. A grid shaped like a thin plate is often used to remove the scattered rays. This grid is disposed between an object and a radiation imaging apparatus, preferably, disposed right in front of the radiation imaging apparatus. The grid has, for example, a stripe structure in which a strip-shaped radiation transmissive layer and a strip-shaped radiation absorption layer that extend in the column direction of pixels are alternately arranged in the row direction of the pixels.

In a case where the relative positions of the grid and the dose detection pixels are displaced from each other, the overlap between the dose detection pixels and the radiation absorption layers can change. Thus, in a case where the relative positions of the dose detection pixels and the grid are displaced from each other, signals for detecting the irradiated dose can greatly vary, which can affect the accuracy of the detected dose.

Japanese Patent Application Laid-Open Publication No. 2014-039792 discusses a radiation imaging apparatus in which the relationship between the pitch of repeating patterns of a stripe structure of a grid and the pitch of dose detection pixels in the pitch direction of the grid is defined to be a desired relationship. According to the discussion in Japanese Patent Application Laid-Open Publication No. 2014-039792, even in a case where the positional relationship with the grid is changed by the radiation imaging apparatus, it is possible to reduce variation in the output of the dose detection pixels.

However, in the radiation imaging apparatus of Japanese Patent Application Laid-Open Publication No. 2014-039792, the usable pitch of the grid is limited. This restricts the degree of freedom of a grid selectable for this radiation imaging apparatus, or the degree of freedom of a radiation imaging apparatus selectable for a radiation imaging system in which this grid is installed.

Thus, the present invention is directed to providing a radiation imaging system that can increase the degree of freedom of selectivity with respect to a grid and the accuracy of a detected dose, even in a case where a radiation imaging apparatus having a built-in dose detection pixel for detecting an irradiated dose is used.

SUMMARY OF THE INVENTION

According to an aspect of the present invention, a radiation imaging apparatus includes a pixel array including, in an imaging region where a plurality of pixels for acquiring radiation image data by imaging performed based on emitted radiation is arranged in a matrix, a detection pixel group in which a plurality of detection pixels for detecting a dose of the radiation is arranged in a row direction, and a control unit configured to control the imaging. A grid disposed on a side of the imaging region on which the radiation is incident can be used, the grid having a stripe structure in which a strip-shaped radiation transmissive layer and a strip-shaped radiation absorption layer that extend in a first direction are alternately arranged in a second direction orthogonal to the first direction. The control unit is configured to execute a mode in which the imaging is controlled using signals from the detection pixel group. The radiation imaging apparatus further comprises a determination unit configured to make a determination as to whether the mode is executable by the control unit, based on information about an angle between the row direction and the first direction.

Further features of the present invention will become apparent from the following description of exemplary embodiments with reference to the attached drawings.

BRIEF DESCRIPTION OF THE DRAWINGS

FIG. 6 is a flowchart illustrating an example of a control method including a determination method.

DESCRIPTION OF THE EMBODIMENTS

Embodiments will be described in detail below with reference to the accompanying drawings. A plurality of features is described in the embodiments, but not all of these features are necessarily indispensable to the invention. Further, in the accompanying drawings, identical or similar configurations are assigned the same reference number, and the description thereof will not be repeated. Radiation in the embodiments of the present invention can include, in addition to alpha rays, beta rays, and gamma rays, which are beams formed by particles (including photons) released by radioactive decay, beams having energy equal to or more than those of such beams, e.g., beams having energy equal to or more than X-rays, particle beams, and cosmic rays.

Figure 1:
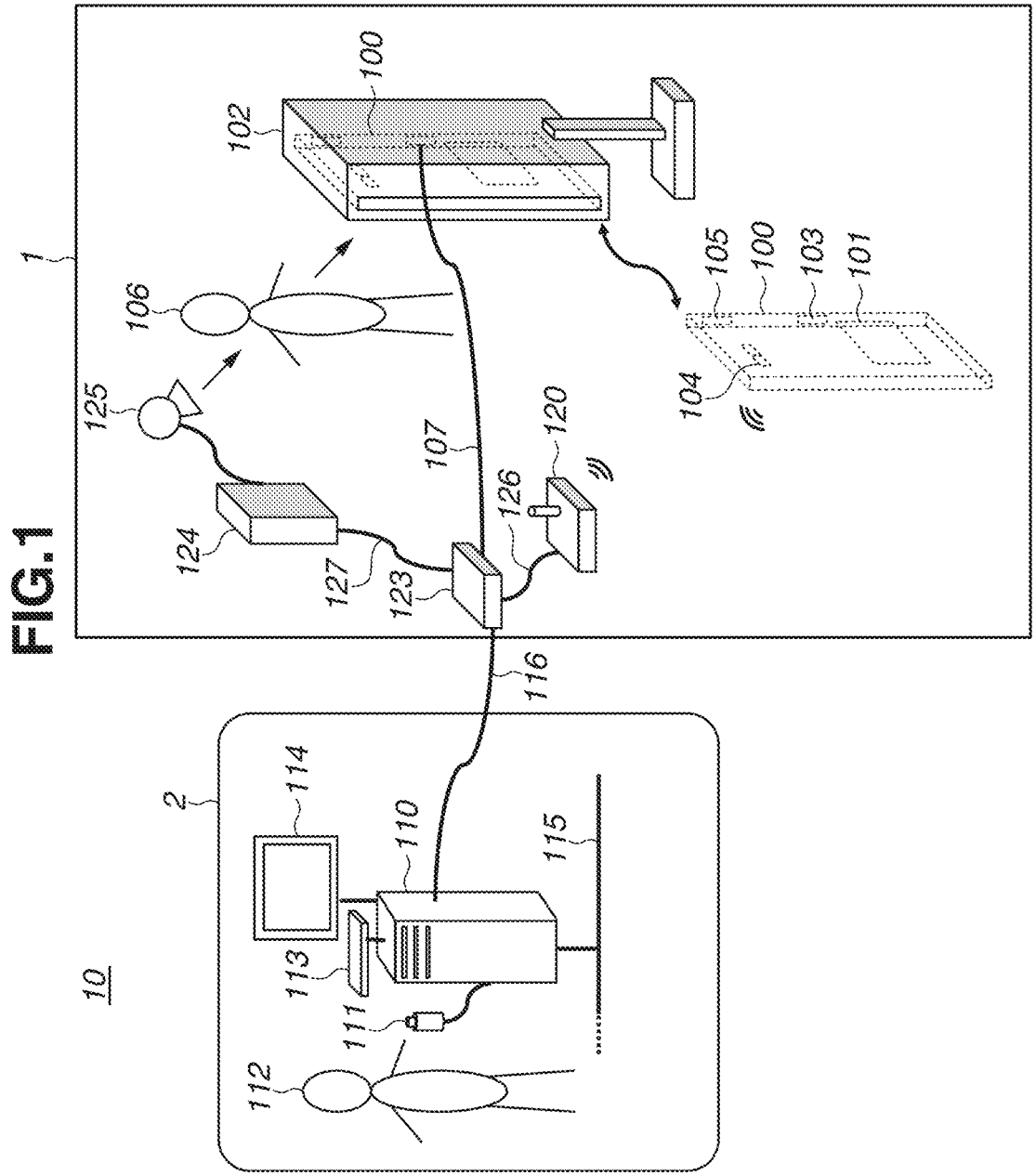
FIG. 1 is a schematic diagram illustrating a configuration example of a radiation imaging system.

FIG. 1 is a diagram illustrating a configuration example of a radiation imaging system 10 according to an embodiment of the present invention. The radiation imaging system 10 has an imaging section 1 and a control section 2. The imaging section 1 performs radiation irradiation and radiation imaging.

The imaging section 1 includes a radiation imaging apparatus 100, a standing position stand 102, a communication cable 107, an access point (AP) 120, a communication control apparatus 123, a radiation control apparatus 124, a radiation source 125, a communication cable 126, and a communication cable 127.

The control section 2 includes a control apparatus 110, a radiation irradiation switch 111, an input device 113, a display device 114, a local area network (LAN) 115, and a communication cable 116.

The radiation imaging apparatus 100 includes a power supply unit 101 including a battery and the like, a wired communication unit 103, a wireless communication unit 104, and an attachment detection unit 105 for detecting attachment to the standing position stand 102. The radiation imaging apparatus 100 performs radiation imaging for a subject 106, by detecting radiation passing through the subject 106, and generating radiation image data.

The wired communication unit 103 communicates information by cable connection using, for example, a communication standard having predetermined protocols, or a standard such as Ethernet. The wireless communication unit 104 has, for example, an antenna and a circuit substrate including an integrated circuit (IC) for communication, and the circuit substrate performs wireless communication processing with a protocol based on a wireless LAN via the antenna. The frequency band, standard, and scheme of the wireless communication in the wireless communication unit 104 are not limited, and a short-range wireless communication scheme such as near-field communication (NFC) or Bluetooth®, or an ultra-wide band (UWB) scheme may be used. The wireless communication unit 104 may have a plurality of wireless communication schemes, and appropriately select the scheme to perform communication.

The attachment detection unit 105 can for instance be implemented by providing a contact-type detection element using a limit switch, a detection element, such as a proximity sensor of magnetic, induction, or electrostatic-capacitance type, or by generating a signal for electrically detecting attachment at the time of the attachment. The attachment detection unit 105 detects the attachment of the radiation imaging apparatus 100 to the standing position stand 102.

The standing position stand 102 is a stand to which the radiation imaging apparatus 100 is attached, so that imaging to obtain a radiation image of a subject in a standing position can be performed. The radiation imaging apparatus 100 can be attached to the standing position stand 102, and can perform imaging in both the attached state and the detached state.

The communication cable 107 is a cable for connecting the radiation imaging apparatus 100 and the communication control apparatus 123. The AP 120 performs wireless communication with the radiation imaging apparatus 100.

For example, the AP 120 is used to relay communication among the radiation imaging apparatus 100, the control apparatus 110, and the radiation control apparatus 124 when the radiation imaging apparatus 100 is detached from the standing position stand 102 and used. The radiation imaging apparatus 100 or the communication control apparatus 123 may have an access point. In such a case, the radiation imaging apparatus 100, the control apparatus 110, and the radiation control apparatus 124 may communicate via the access point of the radiation imaging apparatus 100 or the communication control apparatus 123, without going through the AP 120. The communication control apparatus 123 controls each of the AP 120, the radiation control apparatus 124, and the control apparatus 110 to enable communication thereof.

The radiation control apparatus 124 controls the radiation source 125 to emit radiation based on a predetermined irradiation condition. The radiation source 125 is an irradiation unit that irradiates the subject 106 with radiation, based on the control by the radiation control apparatus 124.

The communication cable 126 is used for connecting the AP 120 and the communication control apparatus 123. The communication cable 127 is used for connecting the radiation control apparatus 124 and the communication control apparatus 123.

The control apparatus 110 communicates with the radiation control apparatus 124 and the radiation imaging apparatus 100 via the communication control apparatus 123, and comprehensively controls the radiation imaging system 10.

The radiation irradiation switch 111 inputs the timing for the radiation irradiation, based on an operation by an operator 112. The input device 113 is a device for inputting an instruction from the operator 112, and includes various types of input devices, such as a keyboard and a touch panel. The display device 114 is a device for displaying radiation image data subjected to image processing and a graphical user interface (GUI), and includes a display. The LAN 115 is a backbone network. The communication cable 116 is a cable for connecting the control apparatus 110 and the communication control apparatus 123.

Figure 2:
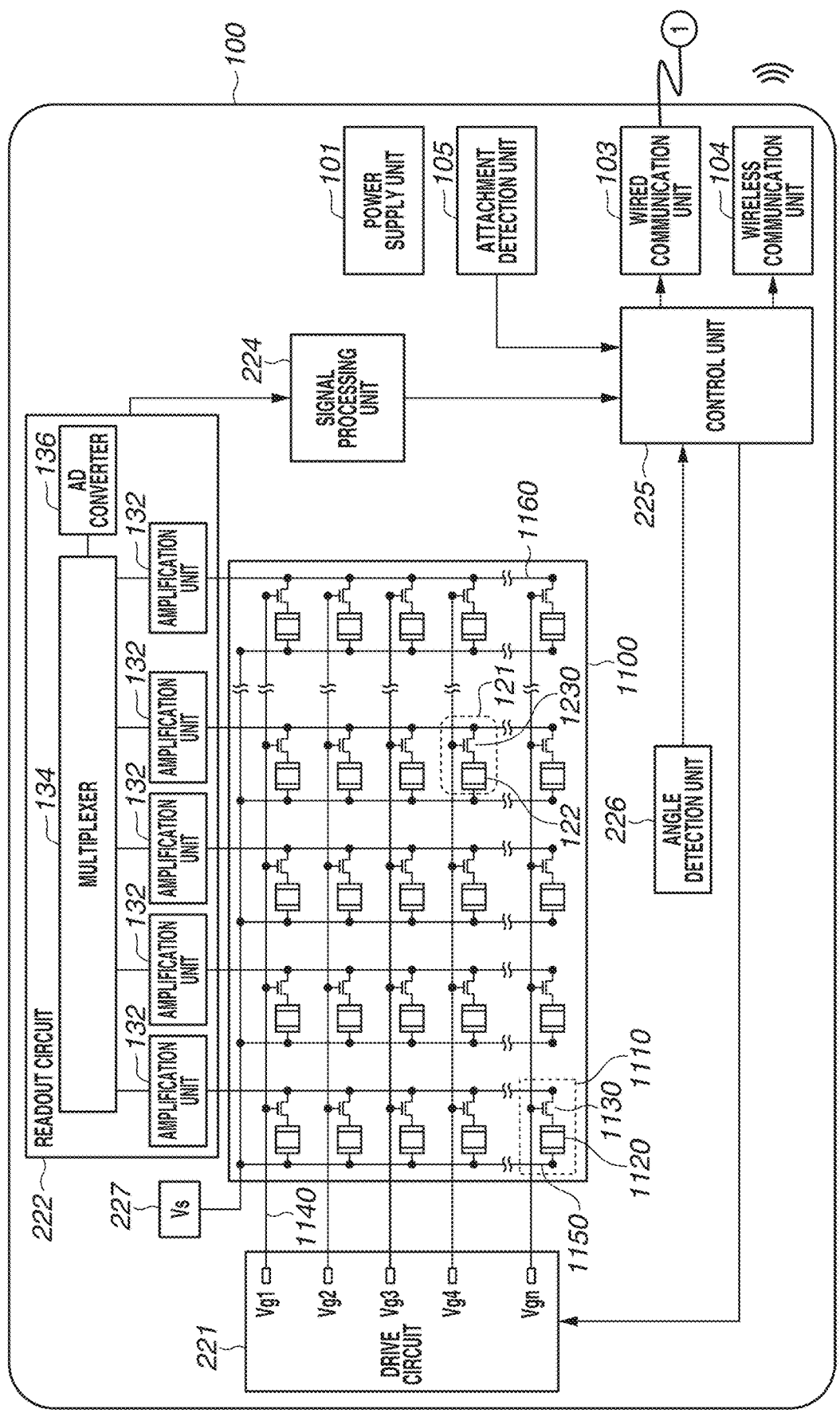
FIG. 2 is a schematic diagram illustrating a configuration example of a radiation imaging apparatus.

FIG. 2 is a diagram illustrating a configuration example of the radiation imaging apparatus 100 in FIG. 1. The radiation imaging apparatus 100 includes a pixel array 1100, a drive circuit 221, a readout circuit 222, a signal processing unit 224, a control unit 225, and a power supply circuit 227, in addition to the power supply unit 101, the wired communication unit 103, the wireless communication unit 104, and the attachment detection unit 105.

The pixel array 1100 has a plurality of pixels arranged in a matrix to acquire radiation image data by imaging in accordance with emitted radiation, and detects the emitted radiation. In the following description, a region where the plurality of pixels is disposed in the pixel array 1100 will be referred to as the imaging region. The plurality of pixels includes a plurality of detection pixels 1110 and a plurality of correction pixels 121, and each convert radiation into an electric signal. The detection pixel 1110 is a pixel for generating a radiation image or detecting a dose of radiation. The correction pixel 121 is a pixel for extracting a dark current component and a crosstalk component.

Each of the plurality of detection pixels 1110 has a conversion element 1120 and a switch 1130. The conversion element 1120 converts radiation into an electric signal. The switch 1130 is provided to connect a column signal line 1160 and the conversion element 1120. The conversion element 1120 has a scintillator for converting radiation into light and a photoelectric conversion element for converting the light into an electric signal, thus converting the radiation into the electric signal. The scintillator is formed like a sheet to cover the imaging region, and shared by the plurality of pixels. The conversion element 1120 may have a conversion element for converting radiation into an electric signal, and thus directly converting the radiation into the electric signal. For example, a thin-film transistor (TFT) in which an active region is formed by a semiconductor, such as an amorphous silicon or polysilicon (preferably, polysilicon), can be used for the switch 1130.

Each of the plurality of correction pixels 121 has a conversion element 122 and a switch 1230. The conversion element 122 has a configuration similar to that of the conversion element 1120, and converts radiation into an electric signal. The switch 1230 has a configuration similar to that of the switch 1130, and is provided to connect the column signal line 1160 and the conversion element 122. The correction pixel 121 has a configuration similar to that of the detection pixel 1110. However, a region for detecting radiation in the detection pixel 1110 is broader than that of the correction pixel 121. For example, in a case where the correction pixel 121 has the conversion element 122 of direct type that directly converts radiation into an electric signal, a shield member with a heavy metal such as lead is disposed on the conversion element 122 of the correction pixel 121, as a shield member for blocking radiation. In a case where the correction pixel 121 has the conversion element 122 of indirect type that converts radiation into light using a scintillator and converts the light into an electric signal, a shield film made of a material such as aluminum is disposed between the conversion element 122 and the scintillator of the correction pixel 121, as a shield member for blocking light. In the correction pixel 121, whether the conversion element 122 is of the direct type or the indirect type, the shield member is disposed in a region at least overlapping a part of the conversion element 122 of the correction pixel 121, in a planar view with respect to the imaging region. The correction pixel 121 blocks radiation, and detects a dark current component or a crosstalk component.

The detection pixels 1110 output radiation dose information or a radiation image based on radiation. The signal processing unit 224 can generate accurate radiation dose information or an accurate radiation image, by subtracting the dark current components or crosstalk components output by the correction pixels 121, from the radiation dose information or radiation image output by the detection pixels 1110.

Figure 3:
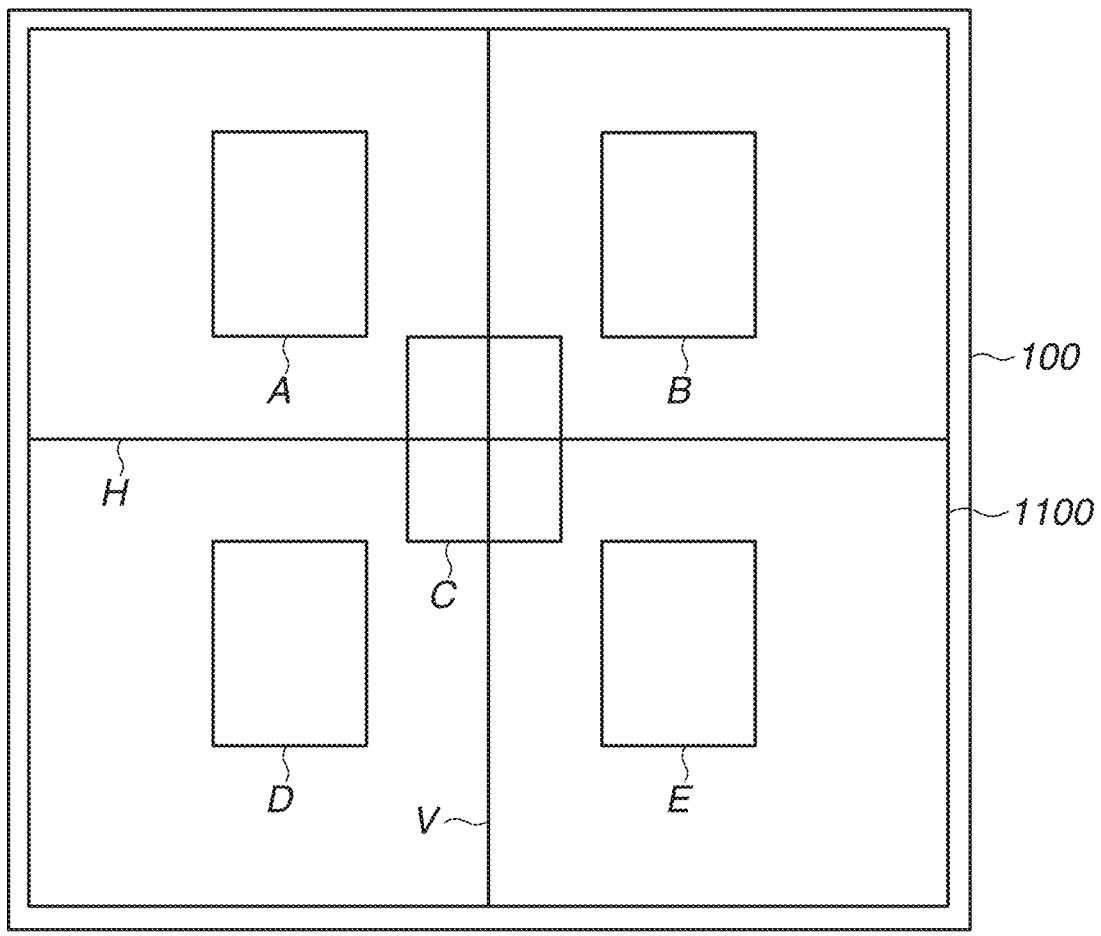
FIG. 3 is a schematic diagram illustrating an example of an arrangement of regions of interest.

FIG. 3 is a diagram illustrating an example of an arrangement of a plurality of regions of interest (ROIs) A to E in the imaging region of the radiation imaging apparatus 100. The pixel array 1100 has detection pixels 1110 and correction pixels 121 in the ROIs A to E, and has detection pixels 1110 in a region other than the ROIs A to E.

The radiation imaging apparatus 100 has a plurality of column signal lines 1160, a plurality of drive lines 1140 and a plurality of bias lines 1150.

Each column signal line 1160 of the plurality of column signal lines 1160 is connected to each pixel of a respective column in the imaging region.

Each drive line 1140 of the plurality of drive lines 1140 is connected to the pixels of a respective row in the imaging region. The drive circuit 221 supplies voltages Vg1 to Vgn to the plurality of pixels row by row via the plurality of drive lines 1140. Here, a direction in which all of the pixels in a row commonly connected to a drive line 1140 are arranged is called the row direction, and a direction in which all of the pixels in a column commonly connected to a column signal line 1160 are arranged is called the column direction. The drive circuit 221 thus drives the plurality of pixels of the pixel array 1100 row by row.

A first electrode of the conversion element 1120 is connected to a first main electrode of the switch 1130. A second electrode of the conversion element 1120 is connected to a bias line 1150. Each bias line 1150 extends in the column direction and is commonly connected to the second electrodes of the plurality of conversion elements 1120 arranged in a respective column in the column direction. A second main electrode of the switch 1130 is connected to a column signal line 1160.

A first electrode of the conversion element 122 is connected to a first main electrode of the switch 1230. A second electrode of the conversion element 122 is connected to a bias line 1150. Each bias line 1150 is commonly connected to the second electrode of the plurality of conversion elements 122 arranged in a column in the column direction. A second main electrode of the switch 1230 is connected to a column signal line 1160.

The power supply circuit 227 supplies a bias voltage Vs to the bias lines 1150. The power supply unit 101 has a battery, a direct current to direct current (DC-DC) converter, and the like. The power supply unit 101 includes the power supply circuit 227, and generates a power supply voltage for an analog circuit, and a power supply voltage for a digital circuit that performs drive control, communication, and the like.

The second main electrode of each of the switches 1130 and 1230 of each column is connected to the column signal line 1160 of the corresponding column A control electrode of each of the switches 1130 and 1230 in each row is connected to a drive line 1140 of the corresponding row. The plurality of column signal lines 1160 is connected to the readout circuit 222.

The readout circuit 222 has a plurality of amplification units 132, a multiplexer 134, and an analog-to-digital converter (hereinafter referred to as the AD converter) 136. The column signal lines 1160 are connected to the respective amplification units 132 (each column signal line 1160 is connected to one amplification unit 132). The amplification unit 132 has, for example, a differential amplifier, and amplifies a signal of the column signal line 1160 using that amplifier. The multiplexer 134 selects the plurality of amplification units 132 in a predetermined order, and supplies a signal from the selected amplification unit 132 to the AD converter 136. The AD converter 136 converts the supplied signal from an analog signal into a digital signal, and outputs the digital signal.

The signal processing unit 224 outputs dose information or a radiation image of radiation irradiating the radiation imaging apparatus 100, based on the output signal of the AD converter 136. Specifically, the signal processing unit 224 subtracts dark current components or crosstalk components generated by the correction pixels 121, from the dose information or radiation image of radiation generated by the detection pixels 1110.

The control unit 225 performs detection of irradiation of radiation, calculation of a dose and an integrated dose of radiation, and the like, based on the information from the signal processing unit 224. The control unit 225 controls the drive circuit 221, the readout circuit 222, and the like, based on the information from the signal processing unit 224 and a control command from the control apparatus 110 in FIG. 1. In other words, the control unit 225 is capable of executing a dose control mode in which imaging performed by the radiation imaging apparatus 100 is controlled, using the dose information of radiation generated using signals from the group of detection pixels 1110 by the signal processing unit 224. The control unit 225 transmits the information from the signal processing unit 224 to the control apparatus 110 via the wired communication unit 103 or the wireless communication unit 104.

Figure 4:
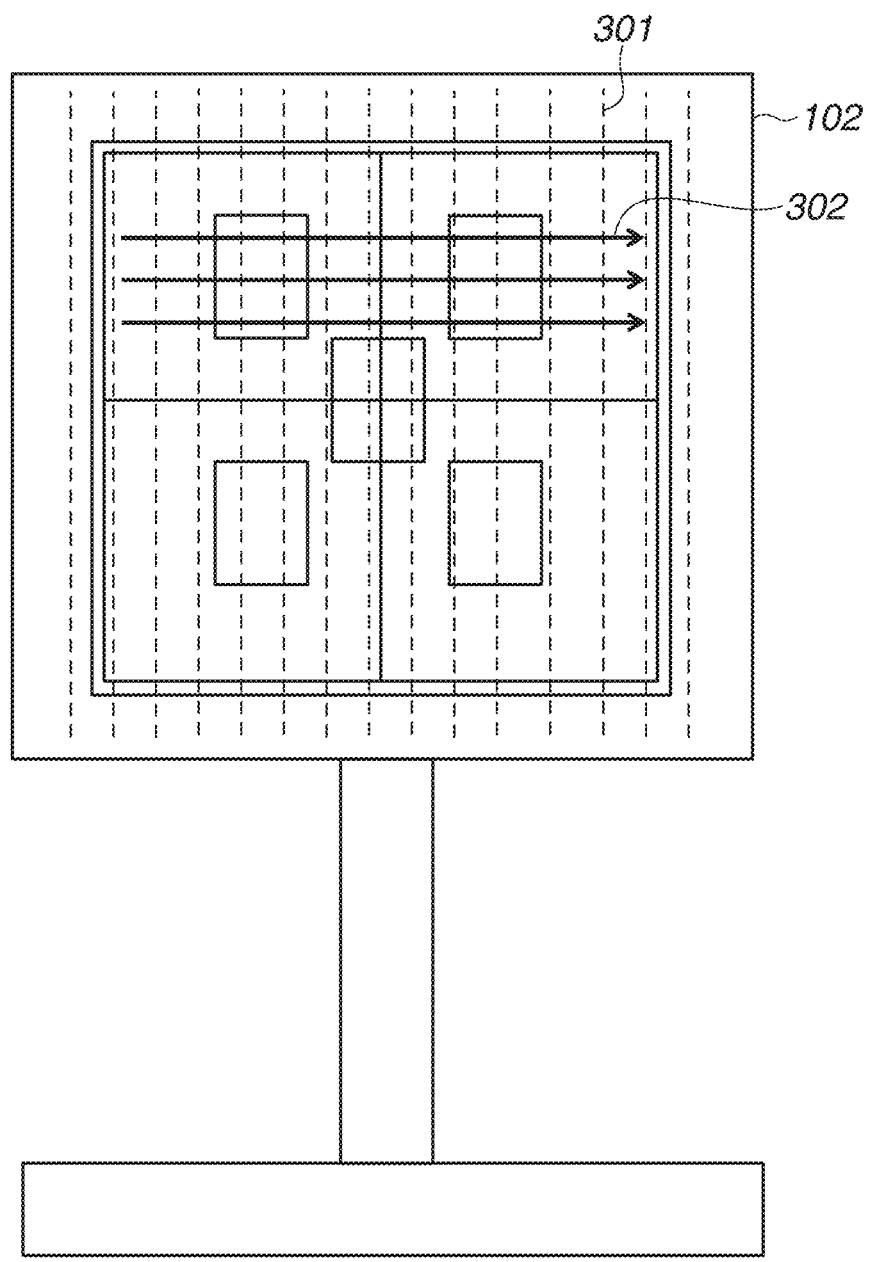
FIG. 4 is a schematic diagram illustrating installation of a grid and a radiation imaging apparatus on a standing position stand.

The radiation imaging apparatus 100 further includes an angle detection unit 226. The angle detection unit 226 is intended to detect an angle of the row direction of the radiation imaging apparatus 100 with respect to the horizontal direction, and an inertial sensor such as an acceleration sensor can be used. As illustrated in FIG. 4, a grid 301 can be mounted on the standing position stand 102. The grid 301 can be installed at the standing position stand 102 to be located on the radiation incident side of the radiation imaging apparatus 100. The grid 301 has a stripe structure in which a strip-shaped radiation transmissive layer and a strip-shaped radiation absorption layer that extend in the vertical direction (a first direction) are alternately arranged in the horizontal direction (a second direction) orthogonal to the vertical direction. Meanwhile, a direction in which a detection pixel group 302, which is a group of the detection pixels 1110 to be simultaneously driven to generate dose information, is arranged is the row direction of the radiation imaging apparatus 100. If the stripe direction of the grid 301 and the array direction of the detection pixel group 302 are substantially orthogonal as illustrated in FIG. 4, the detection accuracy of the dose information can also be secured with respect to the displacement of the grid 301.

However, for example, consider a case where the radiation imaging apparatus 100, which is portable and capable of performing wireless communication, has a rectangular irradiation surface substantially shaped like a square, and which can be attached to the standing position stand 102 even if the radiation imaging apparatus 100, is rotated. In such a case, the first direction in which the stripes of the grid 301 extend and the array direction of the group 302 of the detection pixels 1110 can be substantially parallel. In such a case, it can be difficult to secure the detection accuracy of the dose information with respect to the displacement of the grid 301.

Thus, the control unit 225 determines whether the dose control mode is executable, based on the information about an angle between the row direction, which is the array direction of the detection pixel group 302, and the first direction, which is the stripe direction of the grid 301. Specifically, the control unit 225 determines whether the dose control mode is executable, using an angle $\theta$ of the row direction with respect to the horizontal direction from the angle detection unit 226, as the information about the angle. In a case where the angle $\theta$ is an angle at which the row direction and the first direction can be regarded as being substantially orthogonal (or preferably as being orthogonal), the control unit 225 can determine that the dose control mode is executable. On the other hand, in a case where the angle $\theta$ is not an angle at which the row direction and the first direction can be regarded as being substantially orthogonal, the control unit 225 can determine that the dose control mode is not executable. In a case where the control unit 225 determines that the dose control mode is not executable when executing the dose control mode, the control unit 225 does not control the imaging by the radiation imaging apparatus 100 even if the radiation irradiation switch 111 is pressed. On the other hand, in a case where the control unit 225 determines that the dose control mode is executable when executing the dose control mode, the control unit 225 controls the imaging by the radiation imaging apparatus 100, based on the dose information. Such control enables execution of the dose control mode only in a direction in which the detection accuracy of the dose information can be secured with respect to the displacement of the grid 301, when the radiation imaging apparatus 100 is attached to the standing position stand 102. The degree of freedom of selectivity and the accuracy of the detected dose with respect to the grid 301 can be thereby secured.

An example of a case where an acceleration sensor is used as the angle detection unit 226 will be described. The sensor axial direction of the acceleration sensor and a direction orthogonal to the radiation incident surface of the radiation imaging apparatus 100 are set in a Z-axis, the column direction of the radiation imaging apparatus 100 is set in an X-axis, and the row direction of the same is set in a Y-axis. Based on a signal from the angle detection unit 226 thus set, the angle $\theta$ of the row direction with respect to the horizontal direction can be calculated.

Figure 5:
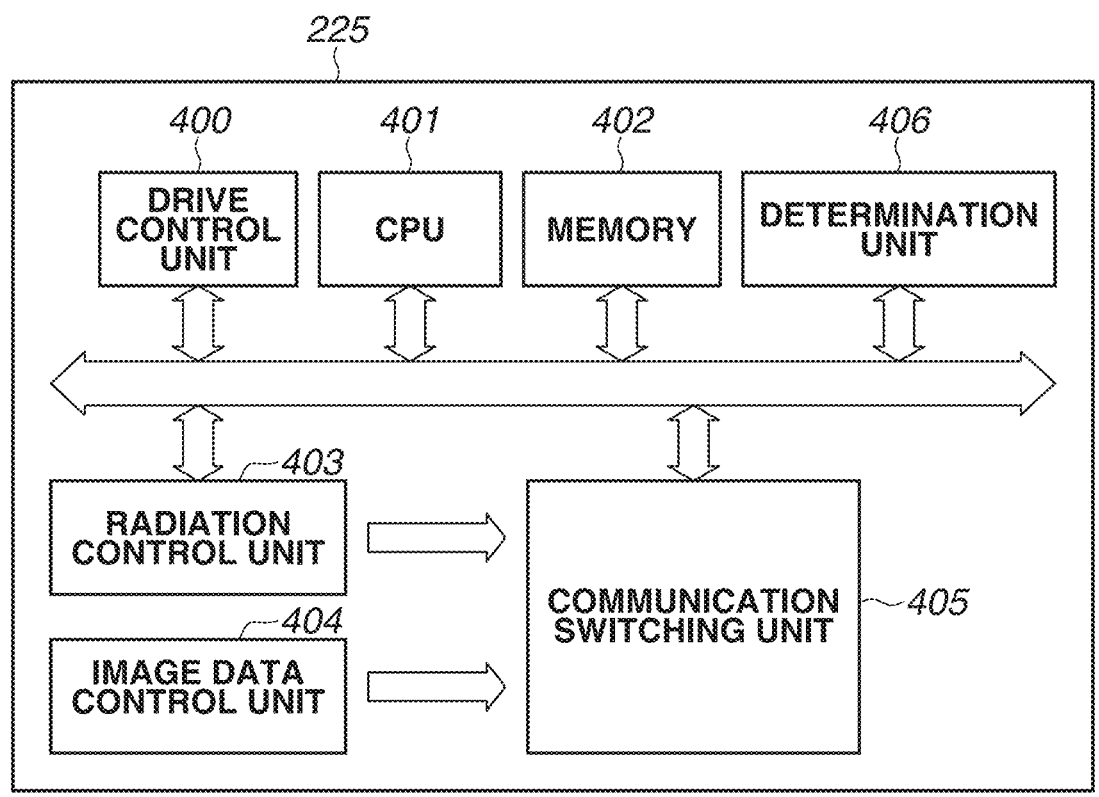
FIG. 5 is a schematic diagram illustrating a configuration example of a control unit.

FIG. 5 is a diagram illustrating a configuration example of the control unit 225 in FIG. 2. The control unit 225 can include a drive control unit 400, a central processing unit (CPU) 401, a memory 402, a radiation control unit 403, an image data control unit 404, a communication switching unit 405, and a determination unit 406.

The drive control unit 400 controls the drive circuit 221 and the readout circuit 222 in FIG. 2, based on information from the signal processing unit 224 in FIG. 2 and a command from the control apparatus 110 in FIG. 1. The CPU 401 performs the overall control of the radiation imaging apparatus 100 using a program and various data stored in the memory 402. The memory 402 stores, for example, a program to be executed by the CPU 401, and various data. The various data includes various data obtained through processing of the CPU 401, and radiation image data.

The radiation control unit 403 controls communication with the radiation control apparatus 124 in FIG. 1, based on information from the signal processing unit 224 in FIG. 2 and information from the drive control unit 400. The radiation control unit 403 and the radiation control apparatus 124 communicate information (e.g., start of irradiation of radiation, notification of stop, and a dose of radiation) about the control of the radiation control apparatus 124 to each other.

The image data control unit 404 stores image data from the signal processing unit 224 in FIG. 2 into the memory 402.

The communication switching unit 405 enables communication by the wired communication unit 103 in a case where the communication cable 107 is connected to the radiation imaging apparatus 100, and enables communication by the wireless communication unit 104 in a case where the communication cable 107 is disconnected from the radiation imaging apparatus 100.

The determination unit 406 determines whether the dose control mode is executable, based on the information about the angle between the row direction, which is the array direction of the detection pixel group 302, and the first direction, which is the stripe direction of the grid 301. Specifically, the determination unit 406 determines whether the dose control mode is executable, using the angle $\theta$ of the row direction with respect to the horizontal direction from the angle detection unit 226, as the information about the angle. In a case where the angle $\theta$ is an angle at which the row direction and the first direction can be regarded as being substantially orthogonal, the determination unit 406 can determine that the dose control mode is executable. On the other hand, in a case where the angle $\theta$ is not an angle at which the row direction and the first direction can be regarded as being substantially orthogonal, the determination unit 406 can determine that the dose control mode is not executable.

Next, operation of the radiation imaging system 10 at the time of automatic exposure control (AEC) imaging will be described. In the AEC imaging, the dose control mode is executed in the radiation imaging apparatus 100. The operator 112 sets subject information, such as the identification (ID), name, and date of birth of the subject 106, and imaging information, such as an imaging site of the subject 106, to the control apparatus 110, using the input device 113.

The operator 112 inputs a dose, a maximum irradiation time, a tube current, a tube voltage, a region of interest, site information, and the like into the control apparatus 110, using the input device 113. The control apparatus 110 transmits the input conditions for irradiation of radiation, region of interest, site information, and the like to the radiation imaging apparatus 100 and the radiation control apparatus 124.

When imaging preparation is completed, the operator 112 presses the radiation irradiation switch 111. When the radiation irradiation switch 111 is pressed, the radiation source 125 irradiates the subject 106 with radiation under the control of the radiation control apparatus 124. In this process, the radiation imaging apparatus 100 communicates with the radiation control apparatus 124 to control the start of the radiation irradiation. The radiation irradiating the subject 106 passes through the subject 106 and is incident on the radiation imaging apparatus 100. The radiation imaging apparatus 100 drives the drive line 1140 designated for each region of interest, by using the drive circuit 221. The plurality of detection pixels 1110 corresponding to the designated drive line 1140 detects a dose (a dose of radiation), and outputs dose information. The control unit 225 of the radiation imaging apparatus 100 calculates an integrated dose, which is an integrated value of doses detected by the detection pixels 1110 in a predetermined period. The control unit 225 of the radiation imaging apparatus 100 calculates a target value of an appropriate dose, from the integrated dose from the signal processing unit 224, the site information and imaging conditions input by the operator 112, and the like, and determines the radiation irradiation stop timing. In a case where the integrated dose reaches the target value, the radiation imaging apparatus 100 transmits a radiation irradiation stop signal to the radiation control apparatus 124 via the communication cable 107, the communication control apparatus 123, and the communication cable 127. The radiation control apparatus 124 stops the irradiation of the radiation of the radiation source 125, based on the received radiation irradiation stop signal. After the irradiation of radiation is stopped, the detection pixel 1110 converts the radiation into an electric signal, and the control unit 225 drives the pixel array 1100 by using the drive circuit 221 in response to the radiation irradiation stop signal. The readout circuit 222 generates a radiation image signal based on the signals from the driven pixel array 1100. The AD converter 136 converts the radiation image signal which is an analog signal into digital radiation image data. The signal processing unit 224 subtracts dark current components or crosstalk components from the radiation image data, and generates corrected radiation image data. The control unit 225 transmits the generated digital radiation image data to the control apparatus 110 via the communication cable 107, the communication control apparatus 123, and the communication cable 116.

The control apparatus 110 subjects the received radiation image data to image processing. The control apparatus 110 displays a radiation image based on the radiation image data subjected to the image processing, on the display device 114. The control apparatus 110 also functions as an image processing device and a display control device.

Here, the example in which imaging is controlled based on a result of comparison between the integrated value of signals from the detection pixel group 302 and the target value serving as a threshold is described, but the present invention is not limited thereto. The control unit 225 may transmit information about the integrated value of signals from the detection pixel group 302 to the radiation control apparatus 124, and the radiation control apparatus 124 may determine the timing for stopping the radiation irradiation by the radiation source 125, based on this information. The control unit 225 may control the imaging based on the integrated value of signals from the detection pixel group 302.

FIG. 6 is a flowchart illustrating a control method of the radiation imaging system 10, and a method of determining whether or not the dose control mode is executable will be described with reference to this flowchart.

In step S501, the operator 112 inputs a dose, a maximum irradiation time, a tube current, a tube voltage, a region of interest, site information, and the like into the control apparatus 110, using the input device 113. The control apparatus 110 transmits the input conditions for irradiation of radiation, region of interest, site information, and the like to the radiation imaging apparatus 100 and the radiation control apparatus 124. The control unit 225 starts imaging preparation of the radiation imaging apparatus 100 so that imaging is executable in the dose control mode. In response to completing the imaging preparation, the control unit 225 transmits a signal indicating the completion of the imaging preparation to the control apparatus 110 and the radiation control apparatus 124, and the operator 112 presses the radiation irradiation switch (SW) 111.

In step S502, the determination unit 406 of the control unit 225 determines whether the dose control mode is executable. The start of the determination to be made by the determination unit 406 may be triggered by the signal indicating the completion of the imaging preparation, or may be triggered by reception of a signal indicating the press of the radiation irradiation switch 111. The determination unit 406 makes the determination, using the angle θ of the row direction with respect to the horizontal direction from the angle detection unit 226, as the information about the angle. In a case where the angle θ is an angle at which the row direction and the first direction can be regarded as being substantially orthogonal, the determination unit 406 determines that the dose control mode is executable (YES in step S502), and the processing proceeds to step S503. On the other hand, in a case where the angle θ is not an angle at which the row direction and the first direction can be regarded as being substantially orthogonal, the determination unit 406 determines that the dose control mode is not executable (NO in step S502), and the processing proceeds to step S504. In this determination, in a case where the absolute value $|\theta|$ of the angle θ is $|\theta| \leq 45°$ or $135° \leq |\theta| \leq 225°$, the determination unit 406 can determine that the angle θ is an angle at which the row direction and the first direction can be regarded as being substantially orthogonal. This makes it possible to perform the determination with less risk of an error and smooth out some movement of the radiation imaging apparatus 100.

If the determination unit 406 determines that the dose control mode is executable (YES in step S502), the processing proceeds to step S503. In step S503, the control unit 225 executes imaging using the radiation imaging apparatus 100 in the dose control mode. On the other hand, if the determination unit 406 determines that the dose control mode is not executable (NO in step S502), the processing proceeds to step S504. In step S504, the control unit 225 cancels imaging using the radiation imaging apparatus 100 in the dose control mode. The control unit 225 transmits a signal indicating the cancellation of the imaging to the control apparatus 110 and the radiation control apparatus 124.

In step S505, the control apparatus 110 displays a notification indicating that the dose control mode is not executable, as an error notification, on the display device 114. In response to the signal indicating the cancellation of the imaging, the radiation control apparatus 124 controls the radiation source 125 so as not to emit radiation even if the radiation irradiation switch 111 is pressed.

Other Embodiments

Embodiments of the present invention can also be implemented by processing for supplying a program for implementing one or more functions of the above-described embodiment to a system or apparatus via a network or storage medium, and causing one or more processors in the computer of the system or apparatus to read and execute the program. An embodiment of the present invention can also be implemented by a circuit (e.g., application specific integrated circuit (ASIC)) that implements the one or more functions.

The above-described embodiments merely represent examples of the embodiment in carrying out the present invention, and the technical scope of the present invention should not be interpreted to be limited to these examples.

According to the embodiments of the present invention, even in a case where a radiation imaging apparatus having a built-in dose detection pixel for detecting an irradiated dose is used, the degree of freedom of selectivity with respect to a grid and the accuracy of a detected dose can be secured.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2021-072810, filed Apr. 22, 2021, which is hereby incorporated by reference herein in its entirety.

What is claimed is:

1. A radiation imaging system comprising:
a pixel array including, in an imaging region where a plurality of pixels for acquiring radiation image data by imaging performed based on emitted radiation is arranged in a matrix, a detection pixel group in which a plurality of detection pixels for detecting a dose of the radiation is arranged in a row direction; and
one or more control units configured to control the imaging,
wherein a grid disposed on a side of the imaging region on which the radiation is incident can be used, the grid having a stripe structure in which a strip-shaped radiation transmissive layer and a strip-shaped radiation absorption layer that extend in a first direction are alternately arranged in a second direction orthogonal to the first direction,
wherein the one or more control units is configured to execute a mode in which the imaging is controlled using signals from the detection pixel group,
wherein the radiation imaging apparatus further comprises a determination unit configured to make a determination as to whether the mode is executable by the one or more control units, based on information about an angle between the row direction and the first direction, and
wherein the one or more control unit is configured not to control the imaging even if the one or more control units receives a signal for issuing the instruction to emit the radiation from a switch for instructing a radiation source configured to emit the radiation to emit the radiation, in a case where the determination unit determines, upon receipt of the instruction, that the mode is not executable.

2. The radiation imaging system according to claim 1, wherein the one or more control units is configured to control the imaging in a case where the determination unit determines, upon receipt of the instruction to emit radiation, that the mode is executable.

3. A radiation imaging system comprising:
a pixel array including, in an imaging region where a plurality of pixels for acquiring radiation image data by imaging performed based on emitted radiation is arranged in a matrix, a detection pixel group in which a plurality of detection pixels for detecting a dose of the radiation is arranged in a row direction;
one or more control units configured to control the imaging,
wherein a grid disposed on a side of the imaging region on which the radiation is incident can be used, the grid having a stripe structure in which a strip-shaped radiation transmissive layer and a strip-shaped radiation absorption layer that extend in a first direction are alternately arranged in a second direction orthogonal to the first direction,
wherein the one or more control units is configured to execute a mode in which the imaging is controlled using signals from the detection pixel group; and
an angle detection unit configured to detect an angle of the row direction with respect to a horizontal direction,
wherein the one or more control units includes a determination unit, and
wherein the determination unit is configured to determine that the mode is executable in a case where the angle of the row direction with respect to the horizontal direction is an angle at which the row direction and the first direction are substantially orthogonal.

4. The radiation imaging system according to claim 3, wherein the determination unit is configured to determine that the angle of the row direction with respect to the horizontal direction is an angle at which the row direction and the first direction are substantially orthogonal and thus the mode is executable, in a case where $|\theta| \leq 45°$ or $135° \leq |\theta| \leq 225°$ is satisfied, where the angle of the row direction with respect to the horizontal direction is $\theta$.

5. The radiation imaging system according to claim 1, further comprising a drive circuit configured to drive the pixel array,
wherein the one or more control units is configured to control the drive circuit, and
wherein the drive circuit is configured to drive the plurality of pixels row by row.

6. The radiation imaging system according to claim 1, wherein the one or more control units is configured to control the imaging based on an integrated value of signals from the detection pixel group in a case where the determination unit determines, upon receipt of an instruction to emit radiation, that the mode is executable.

7. The radiation imaging system according to claim 1, wherein the one or more control units is configured to control the imaging based on a result of comparison between an integrated value of signals from the detection pixel group and a threshold, in a case where the determination unit determines upon receipt of an instruction to emit radiation, that the mode is executable.

8. AThe radiation imaging system according to claim 6, further comprising:
a radiation control apparatus configured to control sa radiation source,
wherein the radiation control apparatus is configured to control the radiation source based on an integrated value of signals from the detection pixel group.

9. AThe radiation imaging system according to claim 7, further comprising:
a radiation control apparatus configured to control a radiation source,
wherein the radiation control apparatus is configured to control the radiation source based on a result of comparison between an integrated value of signals from the detection pixel group and a threshold.

10. The radiation imaging system according to claim 8, further comprising a standing position stand to which the radiation imaging apparatus is attached,
wherein the grid is disposed on a side of the radiation imaging apparatus on which the radiation is incident so that the first direction is parallel to a vertical direction, in the standing position stand.

11. A method for controlling a radiation imaging system including a pixel array including, in an imaging region where a plurality of pixels for acquiring radiation image data by imaging performed based on emitted radiation is arranged in a matrix, a detection pixel group in which a plurality of detection pixels for detecting a dose of the radiation is arranged in a row direction, wherein a grid disposed on a side of the imaging region on which the radiation is incident can be used, the grid having a stripe structure in which a strip-shaped radiation transmissive layer and a strip-shaped radiation absorption layer that extend in a first direction are alternately arranged in a second direction orthogonal to the first direction, the method comprising;
performing control by which a mode in which the imaging is controlled using signals from the detection pixel group is executable,
wherein a determination as to whether the mode is executable based on information about an angle between the row direction and the first direction is made; and
wherein the imaging is not controlled even if a signal is received for issuing the instruction to emit the radiation from a switch for instructing a radiation source configured to emit the radiation to emit the radiation, in a case where the determination unit determines, upon receipt of the instruction, that the mode is not executable.

12. A method for controlling a radiation imaging system including a pixel array including, in an imaging region where a plurality of pixels for acquiring radiation image data by imaging performed based on emitted radiation is arranged in a matrix, a detection pixel group in which a plurality of detection pixels for detecting a dose of the radiation is arranged in a row direction, wherein a grid disposed on a side of the imaging region on which the radiation is incident can be used, the grid having a stripe structure in which a strip-shaped radiation transmissive layer and a strip-shaped radiation absorption layer that extend in a first direction are alternately arranged in a second direction orthogonal to the first direction, the method comprising:
performing control by which a mode in which the imaging is controlled using signals from the detection pixel group is executable;
wherein a determination as to whether the mode is executable based on information about an angle between the row direction and the first direction is made; and
detecting an angle of the row direction with respect to the horizontal direction, and
wherein the mode is executable in a case where it is determined that the angle of the row direction with respect to the horizontal direction is an angle at which the row direction and the first direction are substantially orthogonal.

* * * * *